US009931909B2

(12) United States Patent
McNew

(10) Patent No.: US 9,931,909 B2
(45) Date of Patent: Apr. 3, 2018

(54) AUTOMATED CONTROL OF VEHICLE VENTILATION SYSTEM

(71) Applicant: Toyota Motor Engineering & Manufacturing North America, Inc., Erlanger, KY (US)

(72) Inventor: John-Michael McNew, Ann Arbor, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 0 days.

(21) Appl. No.: 15/208,954

(22) Filed: Jul. 13, 2016

(65) Prior Publication Data

US 2018/0015804 A1    Jan. 18, 2018

(51) Int. Cl.
*B60H 1/00* (2006.01)
*G01N 33/00* (2006.01)
*B60H 3/00* (2006.01)

(52) U.S. Cl.
CPC ......... *B60H 1/008* (2013.01); *B60H 1/00457* (2013.01); *B60H 1/00771* (2013.01);
(Continued)

(58) Field of Classification Search
CPC ............... B60H 1/00771; B60H 1/008; B60H 1/00849; B60H 1/00892; B60H 3/0085; B60H 1/00457; B60H 1/00821
See application file for complete search history.

(56) References Cited

U.S. PATENT DOCUMENTS 4,437,391 A * 3/1984 Eguchi .................. B60H 1/008
165/249
5,670,714 A * 9/1997 Sorensen ........... B60H 1/00764
454/74
(Continued)

FOREIGN PATENT DOCUMENTS

CN       104950708 A    9/2015
DE         4034607 A1    5/1992
(Continued)

OTHER PUBLICATIONS

JPO machine translation of JP 2004-331019 (original JP document published Nov. 25, 2004).*
(Continued)

*Primary Examiner* — Behrang Badii
*Assistant Examiner* — David A Testardi
(74) *Attorney, Agent, or Firm* — Christopher G. Darrow; Darrow Mustafa PC

(57) ABSTRACT

A computing system for a vehicle is provided. The computing system includes one or more processors for controlling operation of the computing device, and a memory for storing data and program instructions usable by the one or more processors, wherein the one or more processors are configured to execute instructions stored in the memory to estimate at least one characteristic of emissions from at least one forward vehicle expected to enter a ventilation system of an ego-vehicle within a predetermined travel distance ahead of the ego-vehicle and, responsive to one or more estimated characteristics, control the ego-vehicle ventilation system.

16 Claims, 4 Drawing Sheets

(52) U.S. Cl.
CPC ..... *B60H 1/00821* (2013.01); *B60H 1/00849* (2013.01); *B60H 1/00892* (2013.01); *G01N 33/0036* (2013.01); *B60H 3/0085* (2013.01)

(56) References Cited

U.S. PATENT DOCUMENTS

| | | | | |
|---|---|---|---|---|
| 5,946,923 | A * | 9/1999 | Samukawa | B60H 1/00764 165/249 |
| 5,980,378 | A * | 11/1999 | Wieszt | B60H 1/008 454/139 |
| 6,168,515 | B1 * | 1/2001 | Daimon | B60H 1/008 165/249 |
| 7,302,339 | B2 | 11/2007 | Gray | |
| 8,649,941 | B1 * | 2/2014 | Tsuda | B60H 1/00771 701/49 |
| 8,854,223 | B2 * | 10/2014 | Cardoso | G01M 15/108 340/463 |
| 2002/0154019 | A1 * | 10/2002 | Kimoto | B60H 1/008 340/632 |
| 2005/0044863 | A1 * | 3/2005 | Maeda | B60H 1/00764 62/125 |
| 2008/0284559 | A1 * | 11/2008 | Biber | B60H 1/008 340/3.9 |
| 2009/0188267 | A1 * | 7/2009 | Dai | B60H 1/00735 62/239 |
| 2009/0326760 | A1 * | 12/2009 | Clark | B60H 1/00771 701/36 |
| 2011/0246022 | A1 * | 10/2011 | Bai | B60H 1/00771 701/36 |
| 2012/0150353 | A1 * | 6/2012 | Bassa | B60H 1/00771 700/276 |
| 2013/0141578 | A1 * | 6/2013 | Chundrlik, Jr. | H04N 7/181 348/148 |
| 2013/0267157 | A1 * | 10/2013 | Park | B60H 1/008 454/70 |
| 2016/0318368 | A1 * | 11/2016 | Alger | B60H 1/00771 |
| 2017/0113512 | A1 * | 4/2017 | Park | B60H 1/00849 |
| 2017/0225537 | A1 * | 8/2017 | Kulthe | B60H 1/00771 |

FOREIGN PATENT DOCUMENTS

| | | | | |
|---|---|---|---|---|
| DE | 102004035882 | A1 * | 2/2006 | ......... B60H 1/00771 |
| DE | 102009041487 | * | 5/2010 | ............. B60H 1/008 |
| EP | 1736769 | A1 * | 12/2006 | ............. B60H 1/008 |
| GB | 2341676 | A * | 3/2000 | ............. B60H 1/262 |
| JP | 04078712 | A * | 3/1992 | |
| JP | 2001101561 | A * | 4/2001 | |
| JP | 2002225541 | A * | 8/2002 | |
| JP | 2002225542 | A * | 8/2002 | |
| JP | 2003335121 | A * | 11/2003 | |
| JP | 2004331019 | A * | 11/2004 | |
| JP | 2008267837 | A * | 11/2008 | ......... G01M 15/108 |
| JP | 2014024427 | A * | 2/2014 | |
| JP | 2015069380 | A * | 4/2015 | |
| WO | WO 2008132999 | A1 * | 11/2008 | ......... G01M 15/108 |

OTHER PUBLICATIONS

EPO machine translation of DE 102009041487 (original DE document published May 20, 2010).*

* cited by examiner

US 9,931,909 B2

AUTOMATED CONTROL OF VEHICLE VENTILATION SYSTEM

TECHNICAL FIELD

The present invention relates to automated control of vehicle ventilation systems and elements thereof.

BACKGROUND

A vehicle traveling along a roadway may pass through varying types and concentrations of emissions from other vehicles. Users may manually control the ventilation system intakes to limit the intake of emissions into the vehicle. As most of these emissions may be invisible, it may be difficult for a driver to determine when the vehicle ventilation system intakes should be closed and/or when the system blower or impeller should be turned off or down. The vehicle may be immersed in a high-concentration emission zone before the driver can react by switching the ventilation system to "recirculate". Also, because the concentrations of emissions in the path of the vehicle are constantly varying, it may be difficult to manually control the ventilation system so as to prevent or limit intake of high concentrations of emissions into the vehicle.

SUMMARY

A computing system for a vehicle is provided. The computing system includes one or more processors for controlling operation of the computing device, and a memory for storing data and program instructions usable by the one or more processors, wherein the one or more processors are configured to execute instructions stored in the memory to estimate at least one characteristic of emissions from at least one forward vehicle expected to enter a ventilation system of an ego-vehicle within a predetermined travel distance ahead of the ego-vehicle and, responsive to one or more estimated characteristics, control the ego-vehicle ventilation system.

In another aspect of the embodiments described herein, a method of controlling a ventilation system of an ego-vehicle is provided. The method includes steps of estimating at least one characteristic of emissions from at least one forward vehicle expected to enter the ego-vehicle ventilation system within a predetermined travel distance ahead of the ego-vehicle and, responsive to one or more estimated characteristics, controlling the ego-vehicle ventilation system.

DETAILED DESCRIPTION

The embodiments described herein relate to a computing system for an ego-vehicle. The system is configured to estimate, using various types of information from a variety of sources, at least one characteristic of emissions from at least one other vehicle whose emissions are expected to enter the ego-vehicle if the ego-vehicle continues on its current path. Based on the estimates, the ego-vehicle automatically controls the ventilation system when the estimated emissions expected to enter the vehicle exceed a predetermined threshold.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Figure 1:
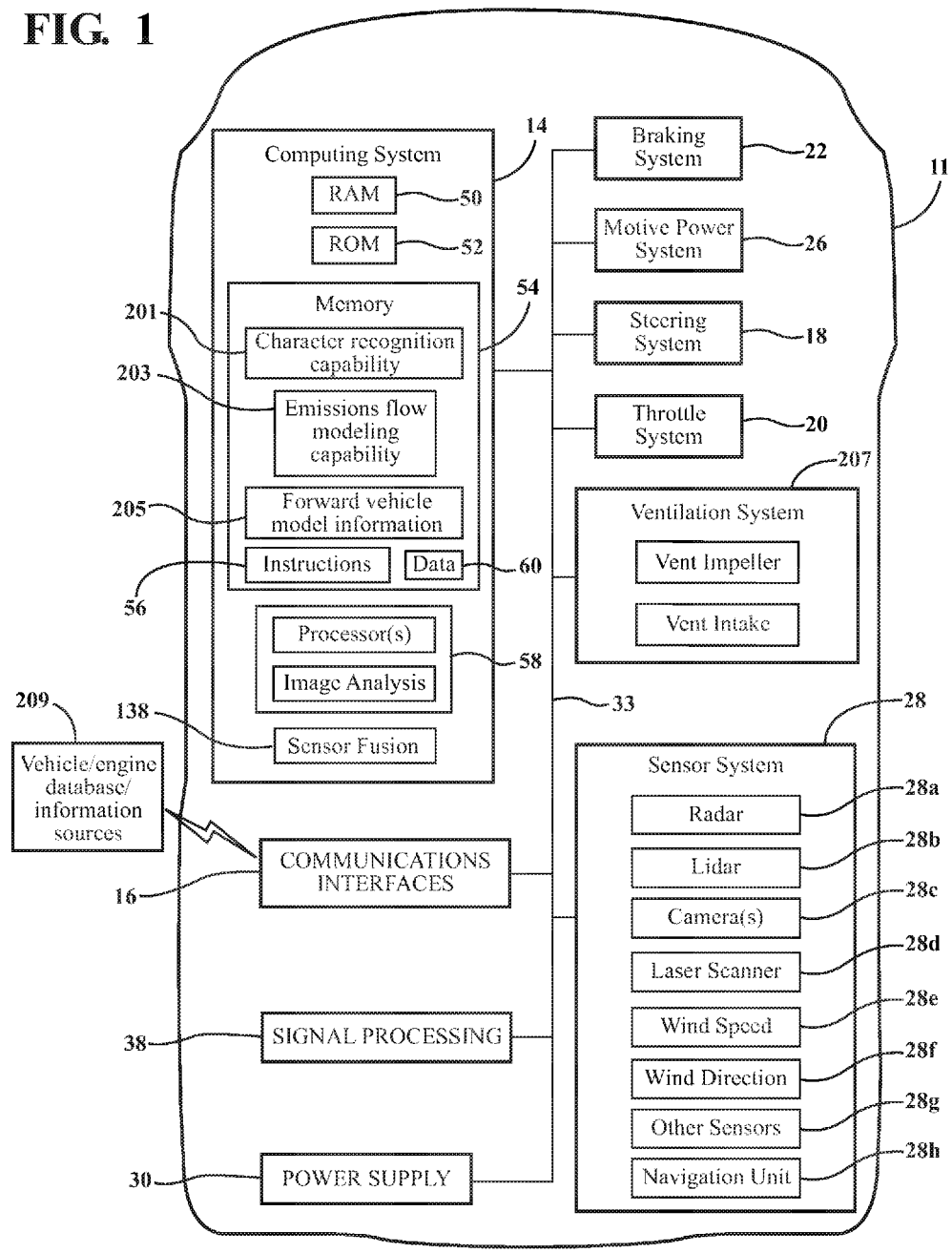
FIG. 1 is a schematic block diagram of a vehicle configured for estimating emissions and controlling a vehicle ventilation system responsive to the emissions estimate, in accordance with one embodiment described herein.

FIG. 1 is a functional block diagram illustrating an ego-vehicle 11 in accordance with an example embodiment. In embodiments described herein, ego-vehicle 11 may be an ego-vehicle, and the various emissions estimation and other vehicle capabilities may be described herein from the perspective of the ego-vehicle 11. The ego-vehicle 11 may include various systems, subsystems and components in operative communication with each other, such as a sensor system or array 28, a computing system 14, one or more communications interfaces 16, a steering system 18, a throttle system 20, a braking system 22, a power supply 30, a motive power system 26, a ventilation system 207, and other systems and components needed for operating the vehicle.

In a known manner, the vehicle sensor system 28 provides data used by the computing system 14 in formulating and executing suitable control commands for the various vehicle systems. The sensor system 28 can include any suitable type of sensor, and vehicle sensors 28 may include any sensors required to support any of the functions described herein. Sensors of the sensor system 28 can be operatively connected to the computing system 14 and/or any other element of the ego-vehicle 11.

The sensor system 28 may include a number of sensors configured to sense information about an external environment of the ego-vehicle 11. For example, the sensor system 28 may include a navigation unit 28h such as a Global Positioning System (GPS), an inertial measurement unit (IMU), a RADAR unit 28a, a laser rangefinder/LIDAR unit 28b, and one or more cameras 28c comprising devices configured to capture a plurality of images of the interior of the vehicle and/or an external environment of the ego-vehicle 11.

Some of sensors 28 may be positioned and/or configured for detecting wind speed (sensor 28e) and wind direction (sensor 28f). For example, the radar unit 28a, the laser rangefinder/LIDAR unit 28b, and/or other sensors may be configured to (in conjunction with other sensors and/or computing system 14) detect or determine the positions of forward vehicles relative to the ego-vehicle 11, the speeds of forward vehicles relative to the ego-vehicle, and the headings of forward vehicles relative to the ego-vehicle. The navigation unit 28h may be configured to estimate a geographic location of the ego-vehicle 11 and also (in conjunction with other sensors and/or computing system 14) the positions and speeds of other, nearby vehicles. To this end, the navigation unit 28h may include a one or more transceivers, including a transceiver operable to provide information regarding the position of the ego-vehicle 11 with respect to Earth. The navigation unit may also be configured to calculate (or aid in calculation of) a route for the vehicle. In a known manner, the navigation unit 28h may also store (or be configured to access) available maps and geographical, topographical, and other information for use in route planning and/or navigation within an area in which the ego-vehicle is travelling. Topographical information may contain grades or slopes, elevations above sea level, and other information relating to the terrain over which the ego-vehicle and surrounding vehicles are currently traversing, and also relating to the terrain in the projected paths of the ego-vehicle and surrounding vehicles.

Vehicle cameras 28c may be positioned and configured to image emission sources (for example, tailpipes) on forward vehicles, to image the rear portions of forward vehicles above the road wheels (for example, to aid in determining the vehicle model name), and to determine the number of axles of a forward vehicle. One or more of the sensors included in the sensor system 28 may also be configured to be actuated separately or collectively in order to modify a position, an orientation, or both, of the one or more sensors. Vehicle cameras 28c may be still cameras or video cameras.

Additional particular types of sensors may include any other types of sensors needed to perform the functions and operations described herein.

Any data collected by vehicle sensors 28 may be transmitted to any vehicle system or component requiring or utilizing the data for the purposes described herein. For example, the data collected by vehicle sensors 28 may be transmitted to computing system 14 or to one or more specialized system or component controllers (not shown).

The ego-vehicle 11 may include a suitable signal processing means 38 for situations where a sensor output signal or other signal requires pre-processing prior to use by the computing system 14 or another vehicle system or element, or where a control signal sent from the computing system will require processing prior to use by actuatable sub-systems or sub-system components (for example, components of the steering system or throttle system). The signal processing means may be an analog-to-digital (A/D) converter or digital-to-analog (D/A) converter, for example.

A sensor fusion algorithm 138 may be an algorithm (or a computer program product storing an algorithm) configured to accept data from the sensor system 28 as an input. The data may include, for example, data representing information sensed at the sensors of the sensor system 28. The sensor fusion algorithm may process data received from the sensor system to generate an integrated or composite signal (formed, for example, from outputs of multiple individual sensors). The sensor fusion algorithm 138 may include, for instance, a Kalman filter, a Bayesian network, or another algorithm. The sensor fusion algorithm 138 may further provide various assessments based on data from the sensor system 28. In an example embodiment, the assessments may include evaluations of individual objects or features in the environment of the ego-vehicle 11, evaluation of a particular situation, and evaluation of possible impacts based on the particular situation. Other assessments are also possible. The sensor fusion algorithm 138 may be stored on a memory (such as memory 54) incorporated into or in operative communication with computing system 14, and may be executed by the computing system in a manner known in the art.

The computing system 14 may continuously receive and process an ongoing or continuous flow of information from sensor system 28 and from other information sources. This information may be processed and/or evaluated in accordance with instructions stored in a memory, in a manner and for the purposes described herein. The use of "continuously" when referring to the reception, gathering, monitoring, processing, and/or determination of any information or parameters described herein means that the computing system 14 is configured to receive and/or process any information relating to these parameters as soon as the information exists or is detected, or as soon as possible in accordance with sensor acquisition and processor processing cycles.

FIG. 1 also illustrates a block diagram of an exemplary computing system according to one or more illustrative embodiments of the disclosure. The computing system 14 may have some or all of the elements shown in FIG. 1. In addition, the computing system 14 may also include additional components as needed or desired for particular applications.

The computing system 14 may control the functioning of the ego-vehicle 11 based on inputs and/or information received from various subsystems (e.g., motive power system 26, sensor system 28, steering system 18, etc.), from any of the communications interfaces 16, and/or from any other suitable source of information. It will be understood that one or more of the functions, methods and/or and capabilities described herein as being performed by the computing system 14 may be performed by a single computing device (for example, by single processors) of computing system 14 or by multiple computing devices (such as multiple ones of processors 58) of computing system 14 arranged in operative communication with each other and operating in a coordinated fashion to perform the desired functions, methods and operations.

The computing system 14 may include one or more processors 58 (which could include at least one microprocessor) for controlling overall operation of the computing system 14 and associated components, and which executes instructions stored in a non-transitory computer readable medium, such as the memory 54. In some embodiments, the computing system 14 may include RAM 50, ROM 52, and/or any other suitable form of computer-readable memory. The memory 54 may comprise one or more computer-readable memories. A computer-readable storage or memory 54 includes any medium that participates in providing data (e.g., instructions), which may be read by a computer. Such a medium may take many forms, including, but not limited to, non-volatile media, volatile media, non-transitory computer readable media, etc. The memory 54 can be a component of the computing system 14, or the memory can be operatively connected to the computing system 14 for use thereby. The term "operatively connected," as used throughout this description, can include direct or indirect connections, including connections without direct physical contact.

The memory 54 may contain data 60 and/or instructions 56 (e.g., program logic) executable by the processor(s) 58 to execute various functions of the ego-vehicle 11. The memory 54 may contain additional instructions as well, including instructions to transmit information to, receive information from, interact with, or control one or more of the vehicle systems and/or components described herein. The memory 54 may also incorporate an emissions flow modeling capability 203 for the purposes described herein. Alternatively, the emissions flow modeling capability 203 may be stored and run in a computing system or device outside the ego-vehicle 11 using information received from the ego-vehicle 11 via a wireless communications system, for example. The results from running the emissions flow model may then be transmitted via wireless to the ego-vehicle computing system 14 for use in controlling the ventilation system 207. The emissions flow modeling capability 203 may be embodied in, for example, an advection-diffusion model or any other computational model usable for predicting or estimating a flow of particulate matter through a fluid. Ego-vehicle sensors incorporated into sensor system 28 may also be configured to detect and measure (or estimate) certain parameters needed as inputs for the emission flow model 203. The inputs and/or data required to run a given emission flow model may depend on the model.

In one or more arrangements, the computing system 14 described herein can incorporate artificial or computational intelligence elements, e.g., neural network, fuzzy logic or other machine learning algorithms. Further, in one or more arrangements, the hardware and/or software elements configured for performing particular functions or operations described herein may be distributed among a plurality of elements and/or locations. In addition to computing system 14, the vehicle may incorporate additional computing systems and/or devices (not shown) to augment or support the control functions performed by computing system 14, or for other purposes.

Communications interfaces 16 may be configured to allow interaction between the ego-vehicle 11 and external sensors, other vehicles, other computer systems, various external messaging and communications systems (such as a satellite system or wireless communication system) and/or a user. The communications interfaces 16 may include a user interface for providing information to or receiving input from a user of the ego-vehicle 11. The communications interfaces 16 may also include interfaces enabling communication in a wide area network (WAN), a wireless telecommunications network, and/or other communications networks. In one or more arrangements, the communication network(s) can include Vehicle-to-Everything (V2X) technologies (including Vehicle-to-Infrastructure (V2I) and Vehicle-to-Vehicle (V2V) technologies), which can allow for communications between any nearby vehicle(s), and the ego-vehicle 11 and any nearby roadside communications nodes and/or infrastructure. When used in a WAN networking environment, the computing system 14 may include (or be operatively connected to) a modem or other means for establishing communications over the WAN, such as network (e.g., the Internet). When used in a wireless telecommunications network, the computing system 14 may include (or be operatively connected to) one or more transceivers, digital signal processors, and additional circuitry and software for communicating with wireless computing devices (not shown) via one or more network devices (e.g., base transceiver stations) in the wireless network. These configurations provide various ways of receiving a constant flow of information relating to vehicle operating conditions from various external sources.

The vehicle ventilation system 207 and elements thereof (such as the vent system impeller, intakes, etc.) are in operative communication with computing system 14 and are configured to be operable responsive to both manual control and to control commands received from the computing system. The vehicle ventilation system 207 may control a rate of flow of air into the vehicle from the vehicle exterior and the flow of air into and through the passenger compartment, by opening, closing or partially closing the ventilation system intakes. The ventilation system may be controlled (by closing the vent intakes) to recirculate air through the passenger compartment or to admit air from the vehicle exterior into the passenger compartment. Actuatable elements of the system include the vent intake(s), the impeller (which may draw outside air into the vehicle or recirculate air already in the vehicle), and the various passenger-operated directional controls which direct airflow to particular portions of the vehicle interior.

The ego-vehicle 11 may be configured so that the computing system 14, sensor system 28, actuatable sub-systems 18, 20, 22, 26 and other systems and elements thereof can communicate with each other using a controller area network (CAN) bus 33 or the like. Via the CAN bus and/or other wired or wireless mechanisms, the computing system 14 may transmit messages to (and/or receive messages from) the various vehicle systems and components. Alternatively, any of the elements and/or systems described herein may be directly connected to each other without the use of a bus. Also, connections between the elements and/or systems described herein may be through another physical medium (such as wired connections) or the connections may be wireless connections.

Figure 2:
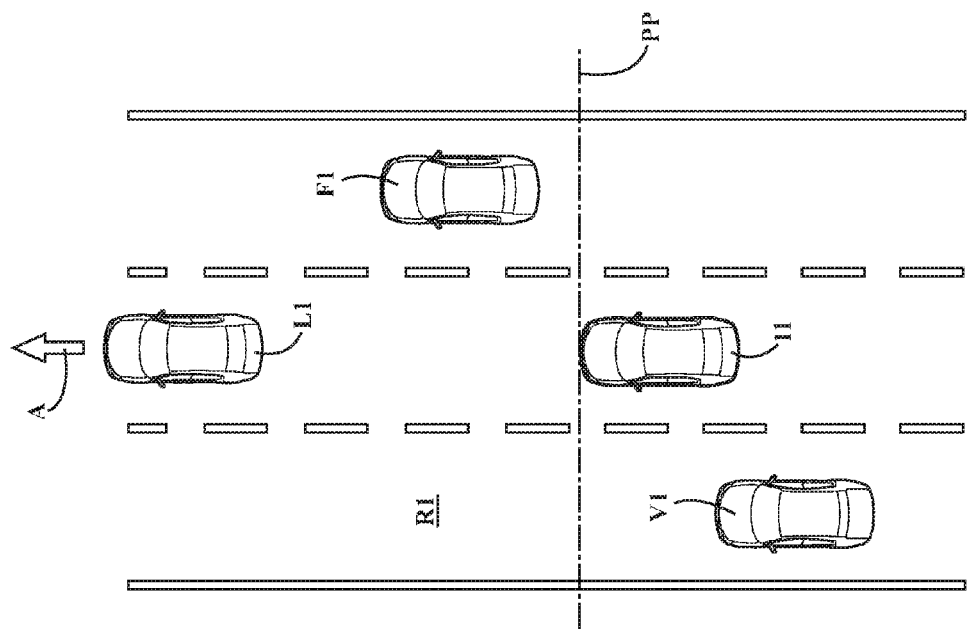
FIG. 2 is a schematic plan view of a portion of a road along which an ego-vehicle and several other nearby vehicles are traveling in a direction "A".

Embodiments of the ego-vehicle 11 described herein may be configured to estimate at least one characteristic of emissions from one or more forward vehicles expected to enter an open vent system of the ego-vehicle 11, and to control the ego-vehicle ventilation system responsive to one or more of the estimated characteristics. FIGS. 2-6 illustrate one method for estimating characteristics of emissions from one or more forward vehicles. Alternative methods may also be employed. FIG. 2 shows a schematic plan view of a portion of a road along which an ego-vehicle 11 and several other nearby vehicles F1, L1 and V1 are traveling in a direction "A". Referring to FIG. 2, for the purposes described herein, a vehicle may be considered to be a "forward vehicle" if the entire vehicle is traveling in front of a vertical plane PP extending through a front-most portion of ego-vehicle 11. This ensures that the vehicle exhaust will be forward of the ego-vehicle plane PP. Forward vehicles are deemed to be traveling ahead of the ego-vehicle, for the purposes described herein. A "leading vehicle" is a forward vehicle which is traveling in the same lane as the ego-vehicle. Thus, for example, on road R1 in FIG. 2, vehicles F1 and L1 are forward vehicles and vehicle L1 is a leading vehicle. For purposes described herein, it may be assumed that emissions from vehicles (such as vehicle V1) located behind plane PP will not reach the vent intakes of ego-vehicle 11 when the vehicles are moving.

Figure 4:
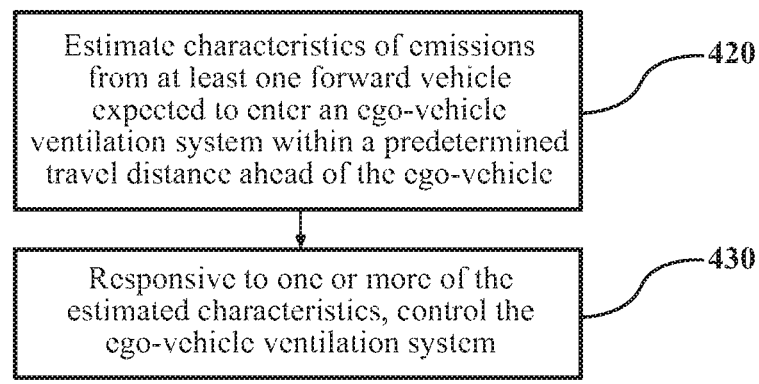
FIG. 4 illustrates one method of estimating characteristics of emissions from one or more forward vehicles expected to enter an open vent system of an ego-vehicle, in accordance with an embodiment described herein.

Referring to FIG. 4, in block 420, the computing system 14 may estimate characteristics of emissions from one or more forward vehicles expected to enter an open vent system of the ego-vehicle 11 within a predetermined travel distance ahead of the ego-vehicle. The emissions may be considered to be any gases, vapors, particulates, and/or other substances exiting a tailpipe or other exhaust of a vehicle. The emissions may, for example, be exhaust emissions of the forward vehicle emitted from one or more vehicle tailpipes or exhaust stacks.

Figure 4A:
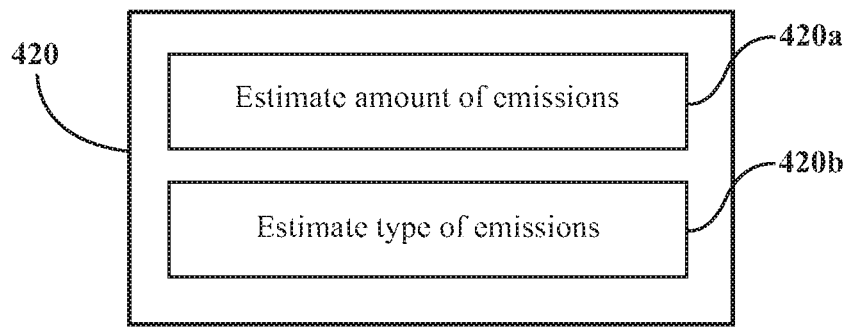
FIG. 4A illustrates one method of estimating at least one characteristic of emissions from at least one forward vehicle expected to enter an ego-vehicle ventilation system within a predetermined travel distance ahead of the ego-vehicle, in accordance with an embodiment described herein.

FIG. 4A illustrates one method of estimating at least one characteristic of emissions from at least one forward vehicle expected to enter the ego-vehicle ventilation system within a predetermined travel distance ahead of the ego-vehicle, as set forth in block 420. In certain embodiments, characteristics of the emissions that are estimated may include at least one of an amount of emissions expected to enter the ego-vehicle ventilation system within the predetermined travel distance ahead of the ego-vehicle (block 420a), and a type of emissions expected to enter the ego-vehicle ventilation system within the predetermined travel distance ahead of the ego-vehicle (block 420b). The ventilation system may be controlled responsive to either or both of these estimated characteristics. For example, if it is desired to prevent a certain type of emissions (such as diesel fumes) from entering the system, the vent system may be closed if any diesel fumes are predicted to enter the system. The blocks 420a and 420b shown in FIG. 4A need not be performed in any particular order. Also, in a given situation, there may be insufficient information available to make all the estimates or determinations set forth in FIG. 4A. The ego-vehicle 11 may be configured to execute as many of the blocks 420a and 420b as possible with the information available. Execution of as many of the blocks as possible may enhance the accuracy of the emissions amount estimate. In some embodiments, the computing system 14 may be configured to make estimations or assumptions regarding missing data or information where necessary to generate the desired estimates.

Figures 5, 6:
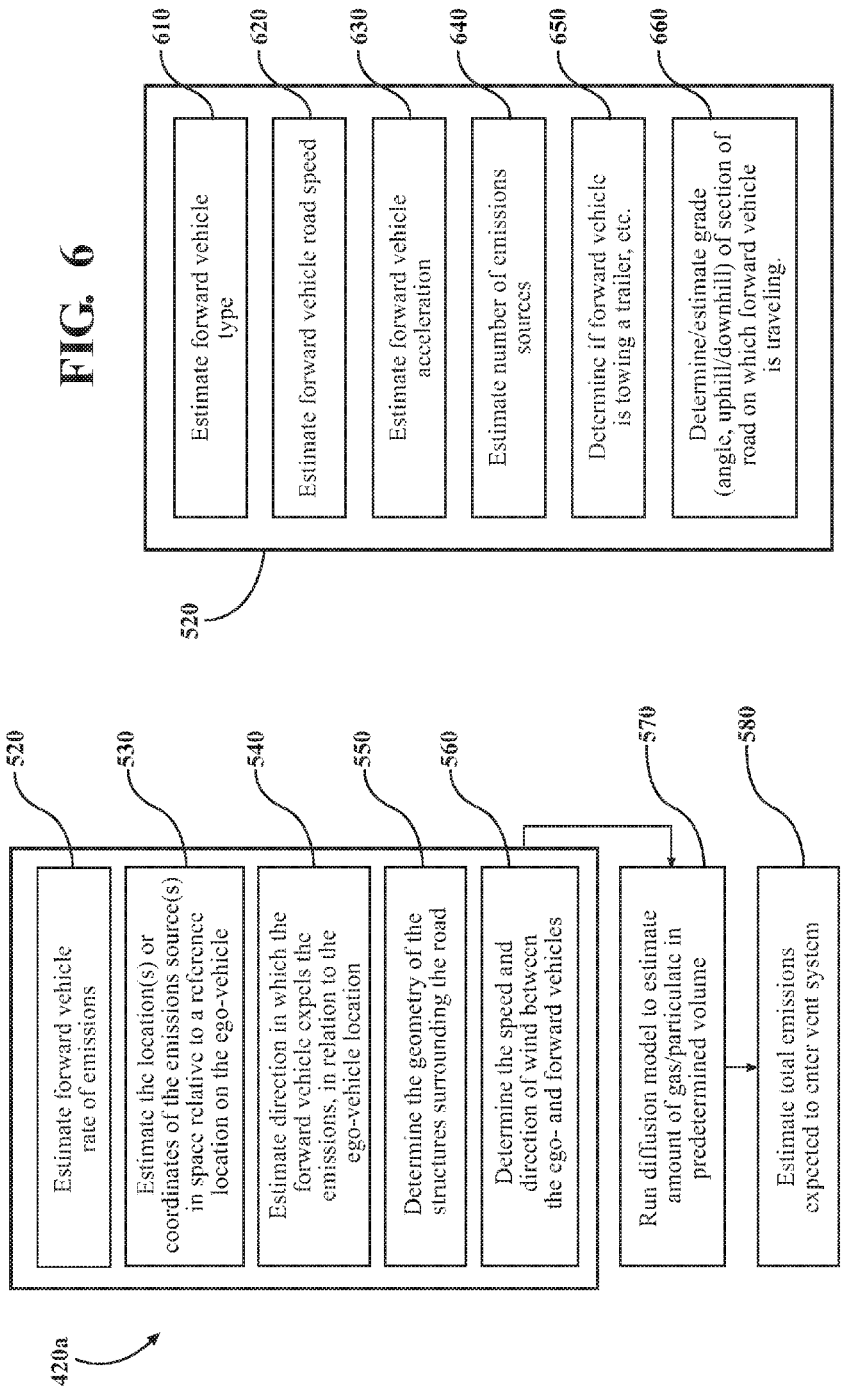
FIG. 5 illustrates one method of estimating an amount of emissions from at least one forward vehicle expected to enter the ego-vehicle ventilation system within a predetermined travel distance ahead of the ego-vehicle, in accordance with an embodiment described herein.
FIG. 6 shows one embodiment of a method of estimating a rate of emissions from at least one forward vehicle, in accordance with an embodiment described herein.

FIG. 5 illustrates one method of estimating an amount of emissions from at least one forward vehicle expected to enter the ego-vehicle ventilation system within a predetermined travel distance ahead of the ego-vehicle, as set forth in block 420a. The various blocks 520-560 shown in FIG. 5 need not be performed in any particular order, and may be performed simultaneously. In addition, in a given situation, there may be insufficient information available to make all the estimates or determinations set forth in FIG. 5. The ego-vehicle 11 may be configured to execute as many of the blocks 520-560 as possible with the information available. Execution of as many of the steps as possible may enhance the accuracy of the emissions amount estimate. In some embodiments, the computing system 14 may be configured to make estimations or assumptions regarding missing data or information where necessary to generate estimates and make determinations. Also, as required, any of the determinations and estimates made in blocks 520-560 may be converted into a form necessary for input into the emissions flow model 203, prior to execution of block 570.

In block 520, a rate of emissions from at least one forward vehicle may be estimated. FIG. 6 shows one embodiment of a method of estimating a rate of emissions from at least one forward vehicle, as set forth in block 520. The various steps shown in FIG. 6 need not be performed in any particular order, and may be performed simultaneously. In addition, in a given situation, there may be insufficient information available to make all the estimates or determinations set forth in FIG. 6. The ego-vehicle 11 may be configured to execute as many of the blocks 610-650 as possible with the information available. Execution of as many of the steps as possible may enhance the accuracy of the emissions rate estimate. In some embodiments, the computing system 14 may be configured to make estimations or assumptions regarding missing data or information where necessary to generate estimates and determinations.

Referring to FIG. 6, the estimated rate of forward vehicle emissions may depend on factors such as the vehicle type, the type of engine, the type of fuel burned, the speed of the forward vehicle, the acceleration of the forward vehicle, the number of emission sources (i.e., tailpipes) on the forward vehicle, and other pertinent factors. In block 610, an estimate may be made as to the vehicle type of the forward vehicle. For example, the forward vehicle may be a passenger sedan, an eighteen-wheel truck, another type of truck, a motorcycle, or a sport utility vehicle (SUV), or another type of vehicle. The type of vehicle may be estimated using data from one or more ego-vehicle sensors, such as radar 28a, lidar or laser scanners 28b, or cameras 28c. Camera images, radar scans, laser scans and/or other sensor data may be processed and interpreted in a known manner to generate a vehicle type in accordance with one of the vehicle types mentioned above and/or other vehicle types, using image analysis processors configured to examine the image data and to identify a forward vehicle classification or model using a vehicle classification algorithm, for example. Alternatively, the type and other characteristics of the forward vehicle may be communicated from the forward vehicle to the ego-vehicle via dedicated short-range communications (DSRC), cellular communications, or via other wireless vehicle-to-vehicle communications.

Information such as the size and/or the shape of the forward vehicle as estimated from camera images or radar scans may be correlated with a known vehicle type stored in an available memory, such as vehicle memory 54. For example, the ego-vehicle computing system 14 may be configured to assume that a vehicle having a height above a certain threshold is a large truck, or that a forward vehicle with a height and width within predetermined ranges is an SUV. In addition, known estimating tools such as probability functions may be used to aid in classifying the forward vehicle using sensor information and/or other available information. The ego-vehicle sensors may also be positioned and configured to detect forward vehicle dimensions and/or shapes from a position behind the forward vehicle (as in the case of vehicle L1 in FIG. 2) and/or from a side of the forward vehicle (as in the case of vehicle F1 in FIG. 2). The ego-vehicle sensors may also be positioned and configured to determine or estimate a number of axles of a forward vehicle, from an image of the forward vehicle traveling in a lane adjacent the lane of the ego-vehicle.

In another aspect, the computing system 14 may incorporate a character recognition capability 201, as shown in FIG. 1. In addition, one or more vehicle of cameras 28c may be positioned and configured to obtain an image of a rear and/or side of a forward vehicle, for purposes of reading a name or other symbol(s) designating a make of the vehicle and/or a model of the vehicle. The computing system may interpret the imaged name or symbol(s) and associate the image with a vehicle model, using a database (such as a vehicle model information source 205) or other source of vehicle model information.

The vehicle model information source 205 may be located in an on-vehicle memory (such as memory 54) or the information source may be located remotely from the vehicle and accessed by computing system 14 via wireless communication (through communications interfaces 16). This source may include vehicle information relating the model of the vehicle to the type of engine, type(s) of fuel burned, any available engine performance curves, emissions information (such as how engine emissions vary with acceleration, for example), the number of tailpipes/emission sources, the location(s) of the emissions sources with respect to the road on the particular vehicle model, and any other vehicle model information pertinent to determination of the vehicle emissions as described herein. The vehicle model information may be in any suitable form, for example, lookup tables, graphs, formulae, etc. The emissions and other information obtained from the vehicle model information source 205 may then be used in estimating the forward vehicle emissions rate. Alternatively, the vehicle type may be determined by any other suitable method.

In blocks 620 and 630, the speed and acceleration of the forward vehicle may be estimated. A forward vehicle traveling at a higher road speed may generate emissions at a greater rate than a vehicle traveling at a lower speed. Also, an accelerating vehicle may generate emissions at a greater rate than a vehicle traveling at a steady speed. The speed and acceleration of the forward vehicle may be estimated by the computing system 14 from ego-vehicle sensor data and/or navigation unit data using known methods.

In block 640, the number of emission sources on the forward vehicle may be estimated. For example, some vehicles may have one tailpipe, while other vehicles have two tailpipes. In one embodiment, computing system 14 may be configured to interpret images from one or more vehicle cameras 28c and/or to interpret other sensor data to determine the location(s) of vehicle emissions sources. Many or most such sources will be visible from the rear and or side of the forward vehicle, and may project from an underside of the forward vehicle. The computing system 14 may be configured to calculate or estimate the spatial locations or coordinates of the forward vehicle emissions sources with respect to a reference location on the ego-vehicle, using sensor information, available forward vehicle information, and/or any pertinent information available from other sources. The reference location may be a vent intake of the ego-vehicle.

In block 650, the ego-vehicle 11 may make (or attempt to make) a determination as to whether a forward vehicle is towing a trailer or another object. The forward vehicle rate of emissions may be greater if the forward vehicle is working harder to tow a trailer. A determination as to whether the forward vehicle is towing a trailer may be made using one or more of the methods previously described (for example, a camera system and image analysis processors, forward vehicle information available from a database, etc.) or from any other suitable information source. For example, cameras in conjunction with image analysis processors and other sensors may be configured to detect the presence of two distinct vehicles traveling at the same speed, in the same lane, one behind the other, and spaced apart at a distance below a certain threshold.

In block 660, the ego-vehicle 11 may determine or estimate the grade or slope of a section of road on which the forward-vehicle is traveling. The grade or slope of the road may affect how hard the forward vehicle engine is working and, consequently, the quantity and composition of the forward vehicle emissions. Determination or estimation of the road grade may be done using information from an on-board ego-vehicle sensor such as an IMU (inertial measurement unit), for example, if the ego-vehicle and the forward vehicle are traveling in such close proximity to each other that the road grade is likely to be the same for both vehicles. Alternatively, the grade information may be determined or obtained from available map or topographical information stored in (or available to) navigation unit 28h, for example.

The above describes some methods and considerations that may be used for estimating a rate of emissions of a forward vehicle. The rate of emissions may alternatively be estimated by any other means suitable for the purposes described herein.

Referring again to FIG. 5, in block 530, the location(s) or coordinates of the forward vehicle emissions source(s) in space relative to a reference location on the ego-vehicle may be estimated. In one embodiment, the reference location is a geometric center of an intake orifice of the ego-vehicle ventilation system, positioned behind the ego-vehicle grille. However, any suitable reference location may be used. For example, emissions from a passenger car traveling in front of and in the same lane as the ego-vehicle may be more likely to enter the ego-vehicle in a greater concentration than emissions from a tractor trailer traveling the same distance in front of the ego-vehicle, because the tailpipe of the passenger car may be much closer to the ego-vehicle vent intakes than the stack of the tractor trailer. The ego-vehicle 11 may be configured to determine the location(s) or coordinates of these emissions sources using one or more of the methods previously described (for example, using sensors such as a camera system and associated image analysis processors, vehicle information available from a database, etc.) or any other suitable method.

In block 540, a direction in which the forward vehicle expels its emissions in relation to the ego-vehicle reference location may be estimated. For example, emissions sources on some forward vehicles may expel emissions in a direction toward the rear of the forward vehicle, while emissions sources on other forward vehicles expel emissions in a direction toward a side of the forward vehicle. The ego-vehicle 11 may receive fewer emissions from a forward vehicle expelling emissions toward a side of the vehicle than would be received from a forward vehicle expelling emissions to a rear of the vehicle. The exhaust direction of the emissions source(s) may be estimated using one or more of the methods and information previously described (for example, using sensors such as a camera system and associated image analysis processors, vehicle information available from a database, etc.) or any other suitable method.

In block 550, the geometry of structures surrounding the road may be determined by any suitable means, for example, by using radar, cameras, image analysis, information from a navigation system, etc. These structures may include walls lining the road, trees, open space, buildings, or other structures. These structures may influence the flow patterns and dispersal of emissions exiting the forward vehicles. For example, if a forward vehicle and the ego-vehicle are driving through a tunnel, the emissions from the forward vehicle may be prevented from dispersing to the degree that they would in a more open environment.

In block 560, the speed and direction of the wind between the forward vehicle and the ego-vehicle 11 may be determined. Wind speed and direction may be determined from suitable ego-vehicle sensors or from other known sources.

In block 570, an emissions flow model (such as model 203 of FIG. 1) configured to estimate the amount of gas/particulate in a predetermined volume of space along the path of the ego-vehicle may be run. Any of the information provided by executing blocks 520 (and including any of blocks 610-650) and 530-560 may be input into the emissions flow model, along with any other pertinent information. Thus, blocks 520 (including blocks 610-650) and 530-560 may be executed prior to running the emissions flow model. The emissions flow model 203 may be configured to calculate and/or estimate a time-dependent dispersal pattern(s) of emissions emanating from the forward vehicle emissions source(s), for example. The emissions flow model 203 and/or the computing system 14 may be configured to look for intersections of the dispersal patterns with a predetermined volume of space ahead of the ego-vehicle along the ego-vehicle route, and also for intersections of the dispersal patterns with other locations along the current projected path of the ego-vehicle.

The measurements, calculations, and/or determinations of the emissions flow model may be made on a continuous basis, depending on such factors as pertinent sensor data acquisition cycle times, wireless connection availability (if needed), and other pertinent factors. The computing system 14 and other pertinent systems may be directed to generating (to the greatest degree possible) constantly updated, real-time estimates of the forward emissions in the current projected path of the ego-vehicle. The lead-time allowable for automatic operation of the vents may need to be adjusted based on the speeds of the ego- and forward vehicles and the pertinent ego-vehicle sensor ranges, due to the fact that the ego-vehicle will cover a greater distance in a given time period when traveling at a relatively greater speed.

In block 580, the total amount of emissions expected to enter the ego-vehicle vent system while traversing a predetermined distance ahead of the ego-vehicle may be estimated. The predetermined distance may be the distance the ego-vehicle will traverse as it passes through a predetermined volume of space (such as volume V1 in FIG. 3, described below) ahead of the ego-vehicle. The computing system may be configured to estimate (based on the results of running the emissions flow model) an amount of emissions from the forward vehicle that will be present within the predetermined volume of space (such as volume V1 in FIG. 3, described below) when the ego-vehicle reaches the predetermined volume. This allows a lead-time for the ego-vehicle vent impeller(s) to be shut down and/or the vent intakes to be closed prior to reaching the predetermined volume, if deemed necessary.

The estimated amount of gas and/or particulates expected to enter the ventilation system may be given in any suitable units. For example, the amount may be determined in units such as ppm, $\mu g/m^3$, or other units. Alternatively, depending on the information available for input into the emissions flow model, a qualitative or relative measure of emissions concentration may be generated and evaluated for purposes of vent system control. That is, in cases where insufficient information exists to formulate a reliable quantitative estimate of emissions for the purposes described herein, the emissions flow model may be configured to make assumptions (based on available information) usable in formulating qualitative estimate(s) of emissions on which ventilation system control commands may be based.

Figure 3:
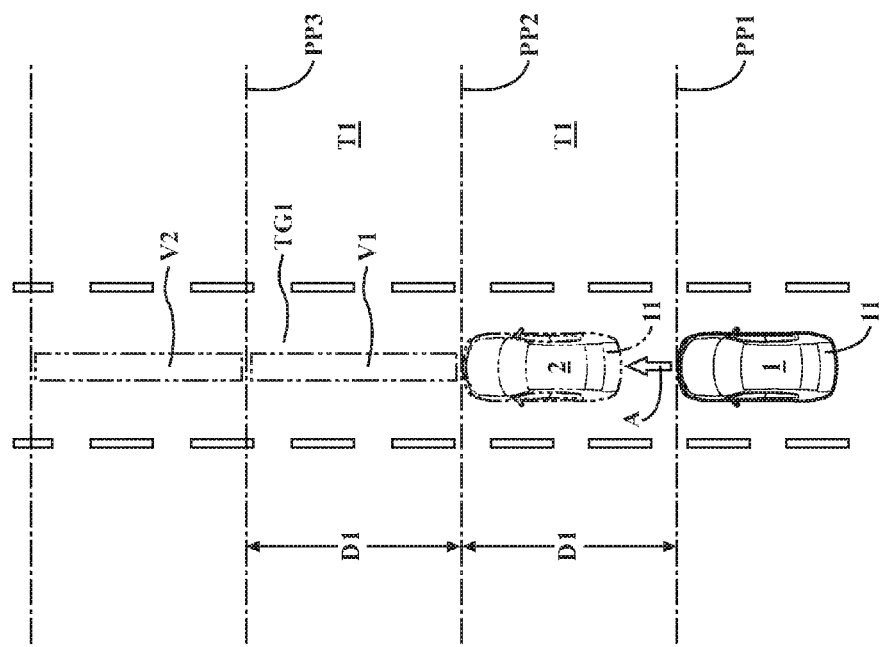
FIG. 3 is a schematic plan view illustrating one method of estimating emissions expected to enter an ego-vehicle along a predetermined route of the ego-vehicle.

Referring to FIG. 3, the predetermined volume V1 may be determined in any desired manner. In one embodiment, it is desired to estimate the emissions in a volume V1 of space located at a distance D1 far enough ahead of the ego-vehicle to allow sufficient time T1 for execution of an acquisition/estimation/control cycle based on the emissions estimate for volume V1. The time required for execution of an acquisition/estimation/control cycle may be the time required to acquire information for estimating an amount of emissions in the volume V1, process the information to formulate an estimate, and operate the ego-vehicle vent intakes and/or operate the vent impeller as needed. Thus, volume V1 for which the emissions are estimated should be far enough ahead of the ego-vehicle to allow the emissions estimate for the volume to be made and appropriate control of the vent system implemented, before the ego-vehicle reaches the volume V1.

In one embodiment, for an ego-vehicle traveling at a constant speed, the volume V1 is a product of an ego-vehicle vent intake area and a distance D1 that the ego-vehicle will travel in a time T1 required to acquire information for estimating an amount of emissions in the volume V1, process the information to formulate an estimate, and operate the ego-vehicle vent intakes and/or operate the vent impeller as needed (i.e., the time required for an acquisition/estimation/control cycle) responsive to the estimated emissions in volume V1. The volume V1 over which the emissions should be estimated may be given by the following relationship:

$$V1 = D1 \times A_{intake} = V_{ego\text{-}vehicle} \times T1 \times A_{intake} \qquad (1)$$

where:
$A_{intake}$=an intake area of the ego-vehicle vent system
$V_{ego\text{-}vehicle}$=the road speed of the ego-vehicle As the ego-vehicle 11 continues to move forward, emissions in successive volumes V2, V3 (not shown), etc. ahead of the ego-vehicle may be estimated so as to provide a continuous, up-to-date estimate of the emissions situation in the projected path of the vehicle. This is illustrated in FIG. 3, in which the road speed of the vehicle is assumed to be constant for purposes of illustration. By the time ego-vehicle 11 is in position 1, the ego-vehicle 11 should begin executing an acquisition/estimation/control cycle for the volume V1, because the vehicle will travel the distance D1 in time T1, and the cycle should be completed before the vehicle reaches the volume V1 in order to ensure that the vent system is in a desired state (i.e. intake(s) open or closed, impeller on or off). Similarly, the acquisition/estimation/control cycle for volume V2 may be executed while the ego-vehicle is traversing volume V1. Thus, the vent system operating state deemed necessary for passage through V2 may be determined and implemented prior to reaching V2. This process may be continued as the ego-vehicle 11 travels along its route.

The capability of the ego-vehicle 11 to estimate the emissions in a volume V1 at a maximum distance from the volume may depend on such factors as sensor capabilities, vehicle speed, the time required for the acquisition/estimation/control cycle, the information required by (and available for) input into the emissions flow model, and other pertinent factors. High sensor ranges and low vehicle speeds will be more conducive to early estimation of emissions in a volume V1 because, at a lower speed, the ego-vehicle will have more time before reaching the volume V1, and relatively high sensor capabilities and ranges will facilitate rapid and complete acquisition of information on which the emissions estimates are based. In case of situations where sensor operability is low enough and/or vehicle speed is high enough (or other conditions are unfavorable enough) so that execution of successive acquisition/estimation/control cycles may not be ensured, the computing system 14 may be configured to make any estimates necessary to execution of the cycle, based on available information. Alternatively, automated control of the vent system may be discontinued and control transferred to the driver, or the vent intakes may simply be automatically closed or left open.

When the amount of emissions in the predetermined volume has been estimated, the amount of emissions predicted to enter the ventilation system during ego-vehicle transit of a predetermined travel distance ahead of the ego-vehicle may be estimated. In one embodiment, the amount estimate may be made based on the assumption that the ego-vehicle intake vent(s) are fully open. In a particular embodiment, the estimated amount of emissions in the predetermined volume of space may be an estimated average gas or particulate content per unit volume multiplied by the predetermined volume. This estimation in a case where the vent impeller is "off" may be different from the estimation when the impeller is "on". For example, for purposes of estimating the emissions that will enter the ego-vehicle ventilation system, it may be assumed that the total amount of gas or particulates TG that will enter the vent intake when passing through the predetermined volume with the vent impeller switched off may be given by the following relationship:

$$TG = V1 \times G1 \quad (2)$$

Where G1=the estimated average amount of gas/particulate in the volume V1.

However, if the ego-vehicle 11 transits the volume V1 with the impeller on, a greater amount of atmosphere may be drawn into the vent intake. Therefore, a greater quantity of emissions may be drawn into the vent system. If it is assumed that all of the atmosphere drawn into the vent intake by the impeller has the same distribution of gas/particulate, then the total gas or particulates TG1 that will enter the vent intake when passing through the predetermined volume V1 when the vent impeller is switched on may be given by the following relationship:

$$TG1 = CFM \times T1 \times G1 \quad (3)$$

where:

CFM=the rate of gas/particulate drawn into the vent system by the impeller;

T1=an amount of time required to transit the volume V1 (i.e., the amount of time required for the vehicle to travel the distance D1); and G1=the estimated average amount of gas/particulate in the volume V1.

The computing system may be configured to, when the impeller is on, assume that the impeller is drawing gas/particulates into the vent system at a rate of CFM during the entire time the ego-vehicle is traversing the volume V1. Thus, with the impeller switched on, a greater amount of atmosphere (and a correspondingly greater amount of gas/particulate) may be drawn into the vent system. Estimates for emissions may be made for both the "impeller on" and "impeller off" cases for purposes of evaluation and/or comparison.

When the emissions predicted to enter the ego-vehicle vent system have been estimated, the estimate may be compared with a predetermined threshold. The threshold may define an allowable amount of emissions in the vehicle passenger compartment, for example. If the emissions predicted to enter the vent system in its current operating state exceed the threshold, the vent system may be controlled to change its operating state. If desired, the emissions estimates determined over any number of successive predetermined volumes may be summed to provide an estimate of the total emissions that may enter the ego-vehicle as the vehicle traverses the volumes. This total may be compared with a threshold, and the result of the comparison may be used to generate suitable control commands. For example, if the threshold is projected to be exceeded, the vent intakes may be closed.

The method just described in one possible method of estimating an amount of emissions expected to enter the vehicle during traversal of the predetermined volume by the ego-vehicle. Other calculation methods and assumptions may also be used.

Referring again to FIG. 4A, the type of emissions from the forward vehicle may be estimated in block 420b. The type of emissions from the forward vehicle may depend on such factors as the type of engine, the type of fuel burned, the operating condition of the engine, and other pertinent factors. Different types of emissions include exhaust from gasoline engines and exhaust from diesel engines, for example. The type of emissions may be estimated from the vehicle type or model, which may be estimated as previously described. The type of emissions may also be estimated from any other available engine or emissions-related information relating to the forward vehicle. An additional source of information relating to various vehicle engines and their performances and emissions at various speeds may be a remotely located vehicle/engine database 209 (FIG. 1), which may be accessed by the computing system when a forward vehicle make, model, and/or type has been identified. Such a database may contain known performance and emissions curves for different types and models of engines.

Referring again to FIG. 4, in block 430, responsive to the estimated type of emissions and/or the total emissions expected to enter the ego-vehicle vent system while traversing a predetermined distance, the computing system may control the ego-vehicle ventilation system. The ventilation system may be controlled by opening or closing the vent intake(s) as desired. The ventilation system may also be controlled by turning the vent impeller one or off as desired.

In a particular embodiment, both the estimated emissions predicted to enter the ego-vehicle with the impeller on and the estimated emissions predicted to enter the ego-vehicle with the impeller off may be determined, for comparison purposes. For example, if the impeller is currently "on", the estimated emissions intake with the impeller left on as the ego-vehicle transits the predetermined volume exceeds the threshold, and the estimated emissions intake with the impeller shut off prior to reaching the predetermined volume is predicted to be below the threshold, then the impeller may be shut off and the vent intakes left open prior to reaching the predetermined volume. If the impeller is currently "on", the estimated emissions intake with the impeller left on exceeds the threshold, and the estimated emission intake with the impeller shut off prior to reaching the predetermined volume is predicted to also be above the threshold, then the vent intakes may be closed prior to reaching the predetermined volume. In this case, the ventilation system would be in a "recirculation" mode. If the impeller is currently "on", and the estimated emissions intake with the impeller left on is predicted to be below the threshold, then the impeller may be left on during transit of the predetermined volume.

Also, the computing system may be configured to apply an increased weight to a certain type of emissions when controlling the vent system. For example, if the estimated emissions are diesel exhaust, the system may control the vent system so that a smaller total amount of emissions are permitted to enter the vent system than would be allowed if the emissions are passenger car exhaust.

Information not directly available (for example, through interpretation of vehicle sensor data, from databases, etc.) for the purposes described herein may be estimated. Qualitative estimations and/or relative values of the various parameters may be made based on such factors as vehicle type, vehicle size, speed, acceleration, and other factors. For example, the computing system 14 may be configured to assume, for computational purposes, that a larger vehicle will generate a higher quantity of emissions than a smaller vehicle traveling at the same speed.

The computing system 14 may be configured to assume, for computational purposes, that an accelerating vehicle will generate a higher quantity of emissions than a vehicle of the same size traveling at a steady speed. The computing system 14 may be configured to assume, for computational purposes, that a vehicle with a diesel engine will generate a higher quantity of emissions than vehicle of the same size or type with a gasoline engine. Assumptions, relationships, and/or information used by the computing system 14 for computational purposes may be expressed and saved in, for example, algorithms, functions, lookup tables, or in any other suitable form. The computing system may also be configured to, if one or more elements of information deemed necessary for the estimates or determinations described herein are not available and cannot be estimated, discontinue automated control of the vent system as described herein.

The procedures described above may be applied to any number of forward vehicles within the ranges of the pertinent ego-vehicle sensors. That is, the pertinent information may be gathered and parameter values determined for estimation of the emissions from each vehicle of multiple forward vehicles. Each of these vehicles may provide a component of the total emissions concentration present at the predetermined location in front of the ego-vehicle at the designated time. These components may be added or otherwise integrated or combined to provide the total emissions concentration.

In another embodiment, an amount of emissions expected to enter the vehicle may be estimated for partially-closed ego-vehicle vent intake(s). Partial closure of the vent intake(s) may reduce the amount of emissions entering the ventilation system, due to the reduced intake area through which the emissions may flow. The reduction in emissions may be sufficient to bring the estimated emissions intake below the predetermined threshold previously described. The estimated emissions for partially-closed vent intakes may be compared with the threshold as previously described. The calculations may be performed by controlling the value of a variable representing the intake open area through which emissions can flow into the vent system, without actually varying or controlling the intake open area until a desired intake open area is determined. If the amount of emissions predicted to enter the ego-vehicle vent system exceeds the threshold, the intake open area variable may be adjusted and the estimated emissions recalculated to provide a revised estimate of the emissions expected to enter the vehicle. This process may be performed iteratively until the estimated emissions for a given vent open area fall below the threshold. Then, responsive to the estimated emissions, the vent intakes may be controlled to vary the intake opening area (i.e., to close the vent intake to a certain degree) to achieve the desired vent open area. This procedure provides a degree of graduated or incremental control over operation of the vent intakes, so that the intakes need not necessarily be completely closed to limit the emissions intake to a value below the threshold.

The flow diagrams and block diagrams in the figures illustrate the architecture, functionality, and operation of possible implementations of systems, methods and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processor or processing system or in a distributed fashion where different elements are spread across several interconnected processors or processing systems. Any kind of processor or processing system or other apparatus adapted for carrying out the methods described herein is suited. A typical combination of hardware and software can be a processor or processing system with computer-usable program code that, when being loaded and executed, controls the processor or processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embodied in an application product which comprises all the features enabling the implementation of the methods described herein and, which when loaded in a processing system, is able to carry out these methods.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e. open language). The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g. AB, AC, BC or ABC).

Aspects herein can be embodied in other forms without departing from the spirit or essential attributes thereof. Accordingly, reference should be made to the following claims, rather than to the foregoing specification, as indicating the scope of the invention.

What is claimed is:

1. A computing system for an ego-vehicle, the computing system comprising one or more processors for controlling operation of the computing system, and a memory for storing data and program instructions usable by the one or more processors, wherein the one or more processors are configured to execute instructions stored in the memory to:
estimate an amount of exhaust emissions expelled from at least one forward vehicle and residing in a predetermined volume spaced apart from the ego-vehicle at a location a predetermined distance ahead of a ventilation system intake of the ego-vehicle;
compare the estimated amount of exhaust emissions residing in the predetermined volume to a predetermined threshold; and
if the estimated amount of exhaust emissions residing in the predetermined volume exceeds the predetermined threshold, control the ventilation system intake to at least partially close the ventilation system intake.

2. The computing system of claim 1 wherein the one or more processors are configured to execute instructions stored in the memory to estimate a rate of emissions of the at least one forward vehicle.

3. The computing system of claim 2 wherein the one or more processors are configured to execute instructions stored in the memory to detect a flow of emissions from the at least one forward vehicle toward a side of the at least one forward vehicle, in relation to a reference location on the ego-vehicle.

4. The computing system of claim 2 wherein the one or more processors are configured to execute instructions stored in the memory to determine a geometry of structures surrounding a road on which the at least one forward vehicle and ego-vehicle are traveling.

5. The computing system of claim 2 wherein the one or more processors are configured to execute instructions stored in the memory to determine a speed and direction of wind between the ego-vehicle and the at least one forward vehicle.

6. The computing system of claim 2 wherein the one or more processors are configured to execute instructions stored in the memory to run an emissions flow model configured to estimate an amount of gas/particulate in the predetermined volume of space in the path of the ego-vehicle.

7. The computing system of claim 1 wherein the predetermined distance ahead of the ventilation system intake of the ego-vehicle is an estimated distance that the ego-vehicle will travel in a time required to acquire information for estimating the amount of emissions residing in the predetermined volume, process the information to formulate an estimate of emissions residing in the predetermined volume, and control the ventilation system intake to at least partially close the ventilation system intake responsive to the estimate of emissions residing in the predetermined volume.

8. The computing system of claim 1 wherein the one or more processors are configured to execute instructions stored in the memory to estimate a type of exhaust emissions residing in the predetermined volume, the type of emissions including at least one of exhaust from gasoline engines and exhaust from diesel engines, and wherein the one or more processors are configured to execute instructions stored in the memory to control the ventilation system intake to at least partially close the ventilation system intake responsive to the estimate of the type of emissions.

9. The computing system of claim 1 wherein the predetermined volume is defined by a product of an ego-vehicle vent intake area and an estimated distance that the ego-vehicle will travel in an estimated time required to acquire information for estimating an amount of exhaust emissions in the predetermined volume, process the acquired information to formulate an estimate of the exhaust emissions residing in the predetermined volume, and control the ventilation system intake to at least partially close the ventilation system intake.

10. The computing system of claim 9 wherein the predetermined volume is defined by the relationship:

$$V1 = D1 \times A_{intake} = V_{ego\text{-}vehicle} \times T1 \times A_{intake}$$

where:
$A_{intake}$=an intake area of the ego-vehicle vent system
$V_{ego\text{-}vehicle}$=the road speed of the ego-vehicle,
and D1=a distance that the ego-vehicle will travel in a time T1 required to acquire information for estimating an amount of emissions in the volume V1, process the information to formulate an estimate of the amount of emissions in the volume V1, and control the ventilation system intake to at least partially close the ventilation system intake.

11. A method of controlling a ventilation system of an ego-vehicle, comprising steps of:
estimating an amount of exhaust emissions residing in a predetermined volume spaced apart from the ego-vehicle at a location a predetermined distance ahead of a vehicle ventilation system intake of the ego-vehicle, in a current path of the ego-vehicle;
iteratively:
a) adjusting a value of a variable representing a vent intake open area of a partially-closed ego-vehicle vent intake through which emissions can flow into the vehicle ventilation system;
b) estimating, for the value of the variable representing the vent intake open area of the partially-closed ego-vehicle vent intake, an amount of exhaust emissions predicted to enter the vehicle ventilation system during ego-vehicle transit of the predetermined volume ahead of the ego-vehicle if the ego-vehicle continues on the current path;
c) comparing, to a predetermined threshold, the estimated amount of exhaust emissions predicted to enter the vehicle ventilation system during ego-vehicle transit of the predetermined volume ahead of the ego-vehicle if the ego-vehicle continues on the current path;
repeating steps (a)-(c) until a value of the variable representing the vent intake open area of the partially-closed ego-vehicle vent intake is reached whereby the estimated amount of exhaust emissions predicted to enter the vehicle ventilation system during ego-vehicle transit of the predetermined volume ahead of the ego-vehicle if the ego-vehicle continues on the current path falls below the predetermined threshold; and
controlling the vent intake open area so as to provide the vent intake opening area of the partially-closed ego-vehicle vent intake represented by the value of the variable, whereby the estimated amount of exhaust emissions predicted to enter the vehicle ventilation system during ego-vehicle transit of the predetermined volume ahead of the ego-vehicle if the ego-vehicle continues on the current path falls below the predetermined threshold.

12. The method of claim 11 wherein the step of estimating an amount of emissions residing in the predetermined volume comprises the step of estimating a rate of emissions of at least one forward vehicle.

13. The method of claim 12 wherein the step of estimating a rate of emissions of at least one forward vehicle comprises at least one of the steps of:
estimating a vehicle type of the at least one forward vehicle;
estimating a road speed of the at least one forward vehicle;
estimating an acceleration of the at least one forward vehicle;
estimating a number of emissions sources of the at least one forward vehicle; and
determining if the at least one forward vehicle is towing a trailer or other device.

14. The method of claim 13 wherein the step of estimating a vehicle type of the at least one forward vehicle comprises steps of:

detecting a name or other symbol designating a make of the at least one forward vehicle and/or a model of the at least one forward vehicle;

interpreting the detected name or symbol; and associating the interpreted name or symbol with a vehicle model using a database or other source of vehicle model information.

15. The method of claim 12 wherein the step of estimating an amount of exhaust emissions residing in a predetermined volume spaced apart from the ego-vehicle comprises the step of determining a geometry of structures surrounding a road on which the ego-vehicle is traveling.

16. The method of claim 11 wherein the step of estimating an amount of exhaust emissions residing in the predetermined volume spaced apart from the ego-vehicle at a location a predetermined distance ahead of a vehicle ventilation system intake of an ego-vehicle in a current path of the ego-vehicle comprises the step of detecting a flow of emissions from at least one forward vehicle toward a side of the at least one forward vehicle in relation to an ego vehicle reference location.

* * * * *

UNITED STATES PATENT AND TRADEMARK OFFICE
CERTIFICATE OF CORRECTION

PATENT NO. : 9,931,909 B2  
APPLICATION NO. : 15/208954  
DATED : April 3, 2018  
INVENTOR(S) : John-Michael McNew Page 1 of 1

It is certified that error appears in the above-identified patent and that said Letters Patent is hereby corrected as shown below:

In the Specification

Column 3, Line 6: delete "280" and insert -- 28f) --

Signed and Sealed this  
Eleventh Day of December, 2018

Andrei Iancu  
*Director of the United States Patent and Trademark Office*